US00PP13478P2

(12) United States Plant Patent
Bradford

(10) Patent No.: US PP13,478 P2
(45) Date of Patent: Jan. 14, 2003

(54) PLUM TREE NAMED 'YUMMYBEAUT'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,017

(22) Filed: Dec. 13, 2001

(51) Int. Cl.[7] ..... A01H 5/00
(52) U.S. Cl. ..... Plt./184; Plt./185
(58) Field of Search ..... Plt./184, 185

(56) References Cited

U.S. PATENT DOCUMENTS

PP1,756 P * 9/1958 Anderson ..... Plt./184
PP3,617 P 9/1974 Anderson ..... Plt./184

* cited by examiner

*Primary Examiner*—Bruce R. Campell
*Assistant Examiner*—W C Haas

(57) ABSTRACT

The present invention relates to a plum tree, *Prunus salicina,* and more particularly to a new and distinct variety broadly characterized by a large size, vigorous, hardy, self-unfruitful, usually productive tree. The fruit matures under the ecological conditions described during the third week in June, with first picking on Jun. 17, 2001. The fruit is uniformly medium in size, excellent in flavor, globose in shape, clingstone in type, very firm in texture, yellow in flesh color, and dark red to purple in skin color. The variety was developed as a first generation cross using 'Grand Rosa' (U.S. Plant Pat. No. 1,756) as the selected seed parent and an unnamed plum seedling as the selected pollen parent.

1 Drawing Sheet

BOTANICAL CLASSIFICATION

*Prunus salicina.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of plum tree, which has been denominated varietally as 'YUMMYBEAUT'. The present variety was hybridized by me in 1995, germinated and grown as a seedling on its own root in my greenhouse, and transplanted to a cultivated area of my experimental orchard at Bradford Farms near Le Grand, Calif. in Merced County (San Joaquin Valley). Specifically, the variety was developed from a first generation cross using 'Grand Rosa' (U.S. Plant Pat. No. 1,756) as the selected seed parent and an unnamed plum seedling as the selected pollen parent. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its seed parent, 'Grand Rosa' (U.S. Plant Pat. No. 1,756), by producing dark red plums that are firm in texture, globose in shape, and dark red in skin color, but is very distinguished therefrom and an improvement thereon by ripening about 8 weeks earlier.

The present variety is most similar to 'Black Beaut' (U.S. Plant Pat. No. 3,617), by being self-unfruitful and producing dark red plums that are globose in shape and that mature during the middle of June, but is distinguished therefrom and an improvement thereon by producing an abundance of pollen and by producing fruit that is firmer in texture, sweeter in flavor, and has no red bleeding in the flesh. Being self-unfruitful, the present variety requires an early blooming cross pollinator, such as 'Ambra' (unpatented). Additionally, the present variety's abundance of pollen entices strong bee activity to its blossoms to facilitate pollination, contrary to 'Black Beaut', which produces virtually no pollen.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin County), Calif., and was developed at the state of firm ripe on Jun. 21, 2001, on the original tree during its sixth growing season. All major color code designations are by reference to the Inter-Society Color Council, National Bureau of Standards. Common color names are also used occasionally.

TREE

Size: Large, reaching and maintaining a height of 13' [4 m.] after six growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright and dense.

Form: Trained to a central leader system by pruning.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable early blooming plum, such as 'Ambra' (unpatented).

Bearing: Usually consistent, but some uncertainty exists if inclement weather is encountered during the blooming period.

Trunk:

*Size*.—Medium, reaching a maximum diameter of 4½" [114 mm.] after the sixth growing season.

*Texture*.—Shaggy.

*Bark color*.—Dark grayish brown [62 d.gy.Br] with Moderate orange yellow [71 m.OY] streaking.

*Lenticels*.—Numerous. Color: Deep orange [51 deep O]. Average Size: ¼" [6.4.].

Branches:

*Size*.—Diameter of first scaffold is 1⅞" [48 mm.] measured 12 inches from the central leader, typical of *Prunus salicina,* and dependent upon cultural practices and climatic conditions.

*Texture*.—Smooth on 1st year wood, increasing roughness with age.

*Color*.—1st Year Wood Topside: Moderate reddish brown [43 m.rBr]. 1st Year Wood Underside: Moderate yellow green [120 m.YG]. Older Wood: Dark brown [59 d.Br] with Light brown [57 l.Br] streaking.

*Lenticels*.—Few, very small. Color: Light yellowish brown [76 l.yBr]. Average size: 1/16" [1.6 mm.].

Leaves:

*Size*.—Medium. Average Length: 2⅞" [73 mm.]. Average width: 1⅝" [41 mm.].

*Arrangement*.—Alternate.

*Thickness*.—Medium.

*Form*.—Elliptical.

*Apex*.—Acuminate.

*Base*.—Acute with an average angle of seventy-five degrees.

*Surface*.—Smooth.

*Color*.—Dorsal Surface: Moderate olive geen [125 m.OlG]. Ventral Surface: Moderate yellow green [120 m.YG].

*Margin*.—Finely serrate.

*Venation*.—Pinnately net veined.

*Petiole*.—Average Length: ⅝" [15.9 mm.]. Average Thickness: 1/16" [1.6 mm.]. Color: Dark Grayish red [20 d.gy.R].

*Stipules*.—Number: 2 per leaf, up to 6 per growing tip. Average Length: 5/16" [7.9 mm.]. Color: Light yellow green [119 l.YG] with a Moderate reddish brown [43.0 m.rBr] tinge around the edges.

*Glands*.—Number: 1 to 4. Position: Alternately and oppositely positioned on the petiole and base of blade. Size: Small. Form: Globose. Color: Light yellow green [119 l.YG] with a Grayish red [19 gy.R] tinge in the center.

*Leaf buds*.—Pointed.

Flower buds:

*Hardiness*.—Hardy, with respect to central California winters.

*Diameter*.—Typically 5/32" [4 mm.] 1 week before bloom.

*Length*.—Typically ⅜" [9.5 mm.] 1 week before bloom.

*Form*.—Not appressed.

*Surface*.—Smooth, not pubescent.

*Color*.—White [263 White].

Flowers: Perfect, complete, perigynous, usually a single pistil, typically twenty-four or more stamens, five sepals and petal locations alternately positioned.

*Number per cluster*.—Typically 3 or 4, up to 8.

*Number of petals*.—Five, no double blossoms observed.

*Petal shape*.—Oval.

*Petal margin*.—Slightly wavy toward the base, smooth toward the apex.

*Average petal diameter*.—¼" [6.4 mm.].

*Average petal length*.—⅜" [9.5 mm.].

*Petal apex*.—Rounded.

*Petal base*.—Rounded to slightly cordate.

*Petal color*.—White [263 White].

*Anther color*.—Light orange yellow [70 l.OY].

*Stigma color*.—Light yellow green [119 l.YG].

*Sepal color*.—Light yellow green [119 l.YG] with a Grayish red [19. gy.R] tinge around the edges.

*Sepal length*.—⅛" [3.2 mm.].

*Sepal width*.—⅛" [3.2 mm.].

*Average pistil length*.—5/16" [7.9 mm.].

*Average stamen length*.—5/16" [7.9 mm.].

*Fragrance*.—Moderate when nectar is present.

*Blooming period*.—Early compared with other varieties, a few days after 'Ambra' (unpatented) in 2001.

*Onset of bloom*.—One percent on Feb. 16, 2001.

*Date of full bloom*.—Feb. 26, 2001.

*Duration of bloom*.—One to two weeks, dependent on ambient temperature.

FRUIT

Maturity when described: Firm ripe, Jun. 21, 2001.

Date of first picking: Jun. 17, 2001.

Date of last picking: Jun. 28, 2001.

Size: Uniform, medium.

*Average diameter axially*.—2 5/16" [58.7 mm.].

*Average diameter across suture plane*.—2 5/16" [58.7 mm.].

*Typical weight*.—4.2 ounces [119 grams].

Form: Uniform, symmetrical, globose.

*Longitudinal section form*.—Roundish.

*Transverse section through diameter*.—Roundish.

Suture: An inconspicuous line located in a shallow groove becoming sharper near the base and discontinuing at the apex.

Ventral Surface: Rounded, slightly lipped toward the base.

Lips: Equal.

Cavity: Flaring, circular, suture showing on one side.

*Depth*.—¼" [6.4 mm.].

*Breadth*.—¾" [19.1 mm.].

Base: Truncate.

Apex: Rounded, with a slight hump before and a minor depression beyond the pistil point.

Pistil point: An inconspicuous dot.

Stem: Medium.

*Average length*.—9/16" [14.3 mm.].

*Average width*.—3/32" [2.4 mm.].

Skin:

*Thickness*.—Medium.

*Surface*.—Smooth.

*Tenacity*.—Tenacious to flesh.
*Astringency*.—Astringent.
*Tendency to crack*.—None observed.
*Color*.—Very dark purplish red [260 v.d.pR] to Dark red [16. d.R] where sun protected, with the slightest amount of Moderate yellow [87 m.Y] freckling.
*Bloom*.—Abundant.

Flesh:
*Color*.—Brilliant yellow [83 brill.Y] from the skin to stone on more immature fruits becoming Strong orange yellow [68 s.OY] on fully mature fruit with no bleeding.
*Surface of pit cavity*.—Deep orange yellow [69 deep OY] fibers breaking when twisted from the stone.
*Amygdalin*.—Moderate.
*Juice*.—Very abundant, rich.
*Texture*.—Very firm.
*Fibers*.—Abundant, fine.
*Ripens*.—Slightly earlier toward the apex.
*Flavor*.—Very sweet with moderate acid, 17 to 19 brix.
*Aroma*.—Slight.
*Eating quality*.—Excellent.

STONE

Type: Clingstone.
Form: Oval.
Hilum: Narrow.
Base: Horizontal with a characteristic sharp protrusion located on the dorsal side of the hilum about 3/32" [2.4 mm.] long.
Apex: Forms an average angle of 105 degrees.
Sides: Equal.
Surface: Somewhat rough with a few irregular ridges toward the apex.
Ridges: Sharp, less than 1/32" [0.8 mm.] in height.
Color: Deep orange yellow [69 deep OY].
Average pit wall thickness: 1/16" [1.6 mm.].
Average width: 11/16" [17.5 mm.].
Average length: 1" [25.4 mm.].
Average breadth: 5/16" [7.9 mm.].
Tendency to split: Very slight.
Kernel:
*Form*.—Oval.
*Pellicle color*.—Light grayish yellowish brown [79 l.gy.yBr].
*Skin color*.—Pale yellow [89 p.Y] when first removed.
*Taste*.—Very bitter.
*Viable*.—Yes.
*Average width*.—3/8" [9.5 mm.].
*Average length*.—1/2" [12.7 mm.].
*Amygdalin*.—Abundant.

USE

Market: Fresh market and long distance shipping.
Keeping quality: Excellent. Fruit quality observed to remain in good condition in after 28 days in standard cold room at 36° Fahrenheit [2° Celsius].
Shipping quality: Good.
Resistance to insects: No unusual susceptibilities noted.
Resistance to diseases: No unusal susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Black Beaut' (U.S. Plant Pat. No. 3,617), by being self-unfruitful and producing dark red plums that are globose in shape and that mature during the middle of June, but is distinguished therefrom and an improvement thereon by producing an abundance of pollen and by producing fruit that is firmer in texture, sweeter in flavor, and has no red bleeding in the flesh.

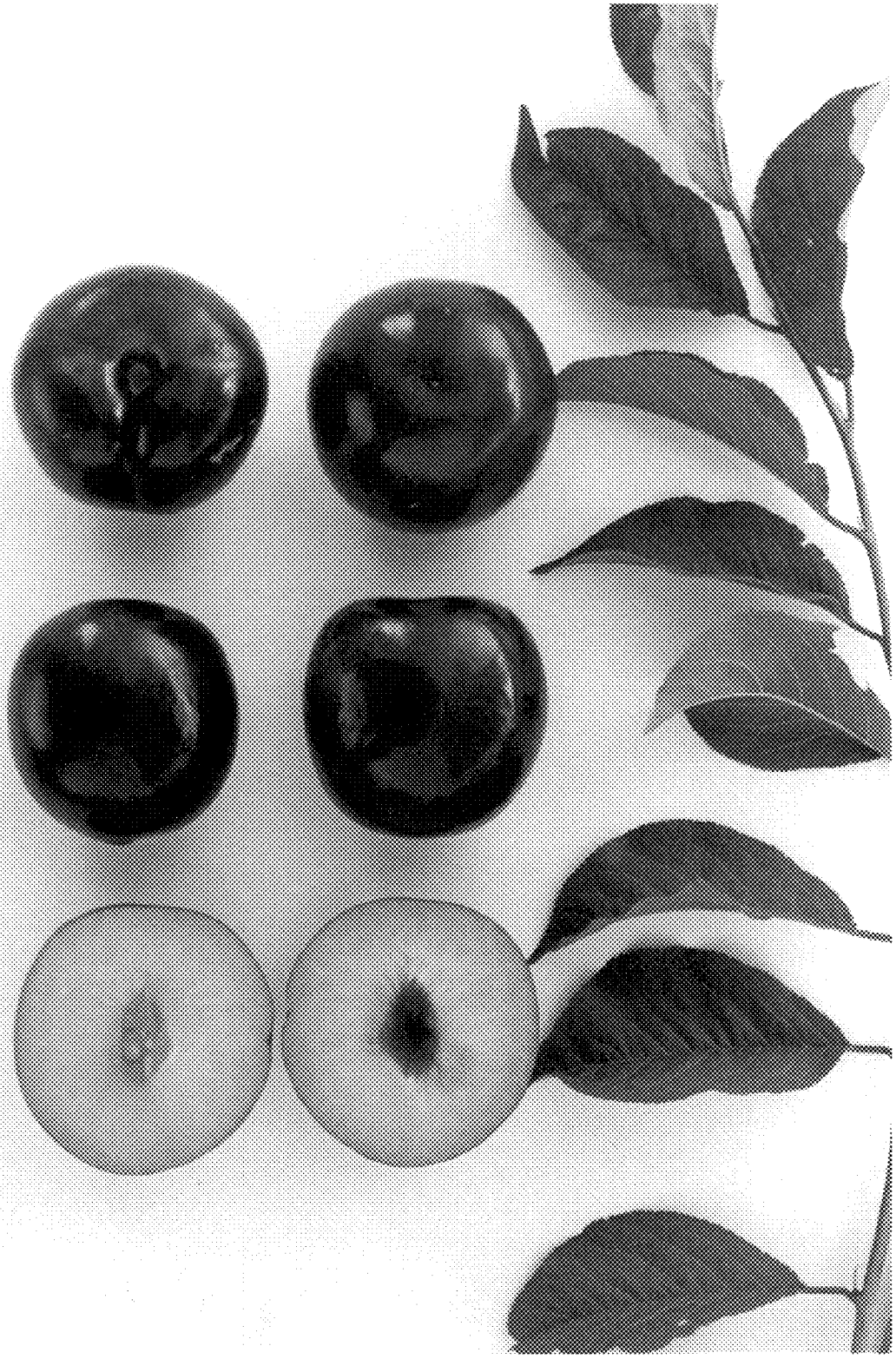

* * * * *